United States Patent
Jain

(10) Patent No.: US 9,023,880 B2
(45) Date of Patent: *May 5, 2015

(54) METHOD OF INHIBITING CONSTITUTIVELY ACTIVE PHOSPHORYLATED FLT3 KINASE

(71) Applicant: AROG Pharmaceuticals, LLC, Dallas, TX (US)

(72) Inventor: Vinay K. Jain, Dallas, TX (US)

(73) Assignee: AROG Pharmaceuticals, LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/026,778

(22) Filed: Sep. 13, 2013

(65) Prior Publication Data

US 2014/0088143 A1   Mar. 27, 2014

Related U.S. Application Data

(60) Provisional application No. 61/704,053, filed on Sep. 21, 2012.

(51) Int. Cl.
| | | |
|---|---|---|
| A61K 31/415 | (2006.01) | |
| A61K 31/47 | (2006.01) | |
| A61K 31/4709 | (2006.01) | |
| A61K 31/4184 | (2006.01) | |

(52) U.S. Cl.
CPC ......... A61K 31/4709 (2013.01); *A61K 31/4184* (2013.01)

(58) Field of Classification Search
CPC . A61K 31/337; A61K 31/4184; A61K 31/47; A61K 31/444; A61K 31/4709
USPC ................................................. 514/394, 314
See application file for complete search history.

(56) References Cited

U.S. PATENT DOCUMENTS

2004/0049032 A1   3/2004   Charrier

FOREIGN PATENT DOCUMENTS

| WO | 02/32861 A2 | 4/2002 |
| WO | 02/092599 A1 | 11/2002 |
| WO | 03/024931 A1 | 3/2003 |
| WO | 03/024969 A1 | 3/2003 |
| WO | 03/099771 A2 | 4/2003 |
| WO | 03/035009 A2 | 5/2003 |
| WO | 03/037347 A1 | 5/2003 |
| WO | 03/057690 A1 | 7/2003 |
| WO | 2004/005281 A1 | 1/2004 |
| WO | 2004/016597 A2 | 2/2004 |
| WO | 2004/018419 A2 | 3/2004 |
| WO | WO 2004020431 A2 * | 3/2004 |
| WO | 2004/039782 A1 | 5/2004 |
| WO | 2004/043389 A2 | 5/2004 |
| WO | 2004/046120 A2 | 6/2004 |
| WO | 2004/058749 A1 | 7/2004 |

OTHER PUBLICATIONS

Takahashi, "Downstream molecular pathways of FTL3 in the pathogenesis of acute myeloid leukemia: biology and therapeutic implications", Journal of Hematology & Oncology, vol. 4, No. 13, pp. 1-10 (2011).*
Abu-Duhier, et al. "FLT3 internal tandem duplication mutations in adult acute myeloid leukemia define a high risk group" British Journal of Haematology. 2000; 111:190-195.
Bacher, et al. "Prognostic relevance of FLT3-TKD mutations in AML: the combination matters-an analysis of 3082 patients" Blood. 2008; 111:2527-2537.
Bains, et al. "FLT3 and NPM1 mutations in myelodysplastic syndromes: Frequency and potential value for predicting progression to acute myeloid leukemia" American Journal of Clinical Pathology. Jan. 2011; 135:62-69.
Bhamidipati, et al. FLT3 mutations in myelodysplastic syndromes(MDS) and chronic myelomonocytic leukemia (CMML). 2012. Journal of Clinical Oncology. Suppl; abstract 6597.
Carter, et al. "Inhibition of drug-resistant mutants of ABL, KIT, and EGF receptor kinases" Proc. Natl. Acad. Sci. USA.2005; 102:11011-11016.
Drexler, et al. Abstract Only: "Expression of FLT3 receptor and response to FLT3 ligand by leukemic cells" Leukemia. 1996; 10:588-599.
Fabian, et al. "A small molecule-kinases interaction map for clinical kinase inhibitors" Nat Biotechnol. 2005; 23:329-336.
Gilliland, et al. "The roles of FLT3 in hematopoiesis and leukemia" Blood. 2002; 100:1532-1542.
Karaman, et al. "A quantitative analysis of kinase inhibitor selectivity" Nat Biotechnol.2008; 26:127-132.

(Continued)

*Primary Examiner* — Kevin E Weddington
(74) *Attorney, Agent, or Firm* — Edwin S. Flores; Chainey P. Singleton; Chalker Flores, LLP

(57) ABSTRACT

The present invention includes a method of inhibiting or reducing deregulated FLT3 tyrosine kinase activity or FLT3 tyrosine kinase expression in a subject with a proliferative disease by administering to the subject having or suspected to have the proliferative disease, a therapeutically or prophylactically effective amount of the compound of Formula I:

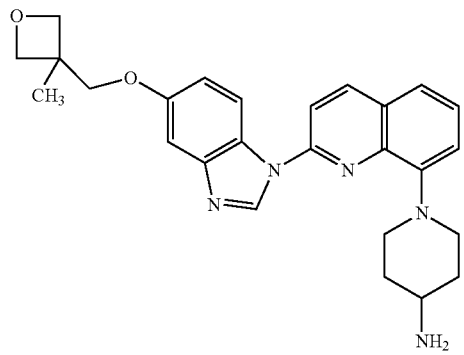

or pharmaceutically acceptable salt thereof.

37 Claims, 6 Drawing Sheets

(56) References Cited

OTHER PUBLICATIONS

Kindler, et al. "FLT3 as a therapeutic target in AML: still challenging after all these years" Blood. 2010; 116:5089-102.

Kiyoi, et al. "Internal tandem duplication of FLT3 associated with leukocytosis in acute promyelocytic leukemia. Leukemia Study Group of the Ministry of Health and Welfare (Kohseisho)" Leukemia. 1997; 11:1447-1452.

Kiyoi, et al. "Internal Tandem duplication of the FLT3 gene is a novel modality of elongation mutation which causes constitutive activation of the product" Leukemia.1998; 12:1333-1337.

Kiyoi, et al. "Prognostic implication of FLT3 and N-RAS gene mutations in acute myeloid leukemia" Blood. 1999; 93:3074-3080.

Kottaridis, et al. "The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials" Blood. 2001; 98:1752-1759.

Liu, et al. "Rational design of inhibitors that bind to inactive kinase conformations" Nature Chem. Biol. 2006; 2:358-354.

Manley, et al. "Advances in the structural biology, design and clinical development of Bcr-Abl kinase inhibitors for the treatment of chronic myeloid leukaemia" Biochim. Biophis. Acta. 2005;1754:3-13.

Muralidhara, et al. "Crenolanib, a novel type I, mutant-specific inhibitor of class III receptor tyrosine kinases, preferentially binds to phosphorylated kinases" Cancer Research. 2012; 72 (8 Supplement): 3683 and Poster.

Nakao, et al. Abstract Only: " Internal tandem duplication of the FLT3 gene found in acute myeloid leukemia. Leukemia" 1996; 10:1911-1918.

Schnittger, et al. "Analysis of FLT3 length mutations in 1003 patients with acute myeloid leukemia: correlation to cytogenetics, FAB subtype, and prognosis in the AMLCG study and usefulness as a marker for the detection of minimal residual disease" Blood. 2002; 100:59-66.

Stirewalt, et al. "The role of FLT3 in haematopoietic malignancies" Nature Reviews Cancer. 2003;3:650-665.

Thiede, et al. "Analysis of FLT3-activating mutations in 979 patients with acute myelogenous leukemia: association with FAB subtypes and identification of subgroups with poor prognosis" Blood. 2002; 99:4326-4335.

Wan, et al. "Mechanism of activation of the RAF-ERK signaling pathway by oncogenic mutations of B-RAF" Cell. 2004;116:855-867.

Yamamoto, et al. "Activating mutation of D835 within the activation loop of FLT3 in human hematologic malignancies" Blood. 2001; 97:2434-2439.

Zhang, et al. "Targeting cancer with small molecule kinase inhibitors. Nature Reviews Cancer" 2009; 9:28-39.

\* cited by examiner

METHOD OF INHIBITING CONSTITUTIVELY ACTIVE PHOSPHORYLATED FLT3 KINASE

CROSS-REFERENCE TO RELATED APPLICATIONS

This application claims priority to U.S. Provisional Application Ser. No. 61/704,053, filed Sep. 21, 2012, the entire content of which is incorporated herein by reference.

TECHNICAL FIELD OF THE INVENTION

The present invention relates to methods of reducing or inhibiting the kinase activity of normal and mutated FLT3 in a cell or a subject, and the use of such methods for preventing or treating cell proliferative disorder (s) related to FLT3.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with protein kinases.

Protein kinases are enzymes that chemically modify other proteins by catalyzing the transfer of gamma phosphates from nucleotide triphosphates, often adenosine triphosphate (ATP), and covalently attaching them to a free hydroxyl group of amino acid residues serine, threonine and tyrosine.

Approximately 30% of all human proteins may be modified by kinase activity. Protein kinases direct the enzymatic activity, cellular location and primary function/association of substrate proteins and regulate cell signal transduction and cell function coordination.

Research studies have shown that aberrant expression of normal or mutated protein kinases are frequently associated with the formation and propagation of a number of diseases. Studies have shown that overexpression or inappropriate protein kinase expression is associated with cancer, cardiovascular disease, rheumatoid arthritis, diabetes, ocular disease, neurologic disorders and autoimmune disease. Thus, investigating compounds that potently inhibit the activity and function of protein kinases will allow for a greater understanding of the physiological roles of protein kinases.

The FMS-like tyrosine kinase 3 (FLT3) gene encodes a membrane bound receptor tyrosine kinase that affects hematopoiesis leading to hematological disorders and malignancies. See Drexler, H G et al. Expression of FLT3 receptor and response to FLT3 ligand by leukemic cells. Leukemia. 1996; 10:588-599; Gilliland, D G and J D Griffin. The roles of FLT3 in hematopoiesis and leukemia. Blood. 2002; 100: 1532-1542; Stirewalt, D L and J P Radich. The role of FLT3 in hematopoietic malignancies. Nat Rev Cancer. 2003; 3:650-665. Activation of FLT3 receptor tyrosine kinases is initiated through the binding of the FLT3 ligand (FLT3L) to the FLT3 receptor, also known as Stem cell tyrosine kinase-1 (STK-1) and fetal liver kinase-2 (flk-2), which is expressed on hematopoietic progenitor and stem cells.

FLT3 is one of the most frequently mutated genes in hematological malignancies, present in approximately 30% of adult acute myeloid leukemia (AML). See Nakao M, S Yokota and T Iwai. Internal tandem duplication of the FLT3 gene found in acute myeloid leukemia. Leukemia. 1996; 10:1911-1918; H Kiyoi, M Towatari and S Yokota. Internal Tandem duplication of the FLT3 gene is a novel modality of elongation mutation, which causes constitutive activation of the product. Leukemia. 1998; 12:1333-1337; P D Kottaridis, R E Gale, et al. The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. Blood. 2001; 98:1742-1759; Yamamoto Y, Kiyoi H, Nakano Y. Activating mutation of D835 within the activation loop of FLT3 in human hematologic malignancies. Blood. 2001; 97:2434-2439; Thiede C, C Steudel, Mohr B. Analysis of FLT3-activating mutations in 979 patients with acute myelogenous leukemia: association with FAB subtypes and identification of subgroups with poor prognosis. Blood. 2002; 99:4326-4335. FLT3 mutations have been detected in approximately 2% of patients diagnosed with intermediate and high risk myelodysplastic syndrome (MDS). See S Bains, Luthra R, Medeiros L J and Zuo Z. FLT3 and NPM1 mutations in myelodysplastic syndromes: Frequency and potential value for predicting progression to acute myeloid leukemia. American Journal of Clinical Pathology. January 2011; 135:62-69; P K Bhamidipati, Daver N G, Kantarjian H, et al. FLT3 mutations in myelodysplastic syndromes(MDS) and chronic myelomonocytic leukemia (CMML). 2012. Journal of Clinical Oncology. Suppl; abstract 6597. Like MDS, the number of FLT3 mutations in patients with acute promyelocytic leukemia (APL) is small. The most common FLT3 mutations are internal tandem duplications (ITDs) that lead to in-frame insertions within the juxtamembrane domain of the FLT3 receptor. FLT3-ITD mutations have been reported in 15-35% of adult AML patients. See Nakao M, S Yokota and T Iwai. Internal tandem duplication of the FLT3 gene found in acute myeloid leukemia. Leukemia. 1996; 10:1911-1918; H Kiyoi, M Towatari and S Yokota. Internal Tandem duplication of the FLT3 gene is a novel modality of elongation mutation, which causes constitutive activation of the product. Leukemia. 1998; 12:1333-1337; H Kiyoi, T Naoe and S Yokota. Internal tandem duplication of FLT3 associated with leukocytosis in acute promyelocytic leukemia. Leukemia Study Group of the Ministry of Health and Welfare (Kohseisho). Leukemia. 1997; 11:1447-1452; S Schnittger, C Schoch and M Duga. Analysis of FLT3 length mutations in 1003 patients with acute myeloid leukemia: correlation to cytogenetics, FAB subtype, and prognosis in the AMLCG study and usefulness as a marker for the detection of minimal residual disease. Blood. 2002; 100:59-66. A FLT3-ITD mutation is an independent predictor of poor patient prognosis and is associated with increased relapse risk after standard chemotherapy, and decreased disease free and overall survival. See F M Abu-Duhier, Goodeve A C, Wilson G A, et al. FLT3 internal tandem duplication mutations in adult acute myeloid leukemia define a high risk group. British Journal of Hematology. 2000; 111:190-195; H Kiyoi, T Naoe, Y Nakano, et al. Prognostic implication of FLT3 and N-RAS gene mutations in acute myeloid leukemia. Blood. 1999; 93:3074-3080. Less frequent are FLT3 point mutations that arise in the activation loop of the FLT3 receptor. The most commonly affected codon is aspartate 835 (D835). Nucleotide substitutions of the D835 residue occur in approximately 5-10% of adult acute myeloid leukemia patients. See DL Stirewalt and J P Radich. The role of FLT3 in haematopoietic malignancies. Nature Reviews Cancer. 2003; 3:650-665; Y Yamamoto, H Kiyoi and Y Nakano, et al. Activating mutation of D835 within the activation loop of FLT3 in human hematologic malignancies. Blood. 2001; 97:2434-2439; C Thiede, Steudal C, Mohr B, et al. Analysis of FLT3-activating mutations in 979 patients with acute myelogenous leukemia: association with FAB subtypes and identification of subgroups with poor prognosis. Blood. 2002; 99:4326-4335; U Bacher, Haferlach C, W Kern, et al. Prognostic relevance of FLT3-TKD mutations in AML: the combination matters-an analysis of 3082 patients. Blood. 2008; 111:2527-2537.

The heightened frequency of constitutively activated mutant FLT3 in adult AML has made the FLT3 gene a highly attractive drug target in this tumor type. Several FLT3 inhibitors with varying degrees of potency and selectivity for the target have been or are currently being investigated and examined in AML patients. See T Kindler, Lipka D B, and Fischer T. FLT3 as a therapeutic target in AML: still challenging after all these years. Blood. 2010; 116:5089-102.

FLT3 kinase inhibitors known in the art include Lestaurtinib (also known as CEP 701, formerly KT-555, Kyowa Hakko, licensed to Cephalon); CHIR-258 (Chiron Corp.); EB10 and IMC-EB10 (ImClone Systems Inc.); Midostaurin (also known as PKC412, Novartis AG); Tandutinib (also known as MLN-518, formerly CT53518, COR Therapeutics Inc., licensed to Millennium Pharmaceuticals Inc.); Sunitinib (also known as SU11248, Pfizer USA); Quizartinib (also known as AC220, Ambit Biosciences); XL 999 (Exelixis USA, licensed to Symphony Evolution, Inc.); GTP 14564 (Merck Biosciences UK); AG1295 and AG1296; CEP-5214 and CEP-7055 (Cephalon). The following PCT International Applications and U.S. patent applications disclose additional kinase modulators, including modulators of FLT3: WO 2002/032861, WO 2002/092599, WO 2003/035009, WO 2003/024931, WO 2003/037347, WO 2003/057690, WO 2003/099771, WO 2004/005281, WO 2004/016597, WO 2004/018419, WO 2004/039782, WO 2004/043389, WO 2004/046120, WO 2004/058749, WO 2004/058749, WO 2003/024969 and U.S Patent Application Publication No. 2004/0049032. See also Levis M, K F Tse, et al. 2001 "A FLT3 tyrosine kinase inhibitor is selectively cytotoxic to acute myeloid leukemia blasts harboring FLT3 internal tandem duplication mutations." Blood 98(3): 885-887; Tse K F, et al., Inhibition of FLT3-mediated transformation by use of a tyrosine kinase inhibitor. Leukemia. July 2001; 15 (7): 1001-1010; Smith, B. Douglas et al., Singlet agent CEP-701, a novel FLT3 inhibitor, shows biologic and clinical activity in patients with relapsed or refractory acute myeloid leukemia Blood, May 2004; 103: 3669-3676; Griswold, Ian J. et al., Effects of MLN518, A Dual FLT3 and KIT Inhibitor, on Normal and Malignant Hematopoiesis. Blood, November 2004; 104 (9): 2912-2918 [Epub ahead of print July 8]; Yee, Kevin W. H. et al., SU5416 and SU5614 inhibit kinase activity of wild-type and mutant FLT3 receptor tyrosine kinase. Blood, October 2002; 100(8): 2941-2949. O'Farrell, Anne-Marie et al., SU11248 is a novel FLT3 tyrosine kinase inhibitor with potent activity in vitro and in vivo. Blood, May 2003; 101(9): 3597-3605; Stone, R. M et al., PKC-412 FLT3 inhibitor therapy in AML: results of a phase II trials. Ann. Hematol. 2004; 83 Suppl 1:S89-90; and Murata, K. et al., Selective cytotoxic mechanism of GTP-14564, a novel tyrosine kinase inhibitor in leukemia cells expressing a constitutively active Fms-like tyrosine kinase 3 (FLT3). J Biol. Chem. Aug. 29, 2003; 278 (35): 32892-32898 [Epub 2003 Jun. 18]; Levis, Mark et al., Small Molecule FLT3 Tyrosine Kinase Inhibitors. Current Pharmaceutical Design, 2004, 10, 1183-1193.

FLT3 inhibitors are classified as Type I or Type II inhibitors. These two classifications are distinguished based on their relative affinities and mechanism of binding to phosphorylated and non-phosphorylated receptor sites. Type I inhibitors recognize the active conformation of kinases. This conformation is conducive to phosphotransfer. Type I inhibitors are generally composed of a heterocyclic ring system. See Liu, Y and N Gray. Rational design of inhibitors that bind to inactive kinase conformations. Nature Chem. Biol. 2006; 2:358-354. Examples of Type I FLT3 inhibitors include Crenolanib besylate and Midostaurin. See Muralidhara C, Ramachandran A, Jain V. Crenolanib, a novel type I, mutant-specific inhibitor of class III receptor tyrosine kinases, preferentially binds to phosphorylated kinases. Cancer Research. 2012; 72 (8 Supplement): 3683; J Cools, et al. Prediction of resistance to small molecule FLT3 inhibitors: implications for molecularly targeted therapy of acute leukemia. Cancer Res. 2004; 64:6385-6389. Resistant mutations that render the kinase of the receptor tyrosine kinase constitutively phosphorylated could potentially be sensitive to type I inhibitors that have greater affinity for the phosphorylated kinase.

By contrast, Type II inhibitors prefer to bind to the inactive conformation of kinases. This conformation is typically referred to as 'DFG-out' owing to the rearrangement of the motif. See J Zhang, Yang P L, and Gray N S. Targeting cancer with small molecule kinase inhibitors. Nature Reviews Cancer. 2009; 9:28-39. Inhibitors such as imatinib, sorafenib and nilotinib bind in the type II conformation. See P W Manley, Cowan-Jacob S W, Mestan J. Advances in the structural biology, design and clinical development of Bcr-Abl kinase inhibitors for the treatment of chronic myeloid leukaemia. Biochim. Biophis. Acta. 2005; 1754:3-13; PT Wan, et al. Mechanism of activation of the RAF-ERK signaling pathway by oncogenic mutations of B-RAF. Cell. 2004; 116:855-867. Resistant mutations to Type II inhibitors are mutations that render the kinase domain of the receptor tyrosine kinase constitutively phosphorylated. Type I inhibitors that target the phosphorylated kinase can overcome the resistance resulting from the treatment with Type II inhibitors, and therefore have potential use in treating diseases that harbor these resistance mutations.

SUMMARY OF THE INVENTION

The present invention includes a method of inhibiting or reducing deregulated FLT3 tyrosine kinase activity or expression in a subject with a proliferative disease which comprises administering to the subject having or suspected to have the proliferative disease, a therapeutically or prophylactically effective amount of the compound of Formula I:

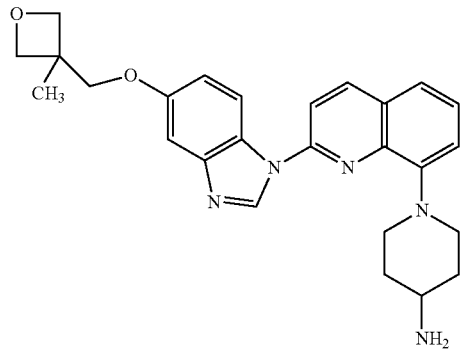 [SMILES: CC1(COc2ccc3c(c2)ncn3-c2ccc3cccc(N4CCC(N)CC4)c3n2)COC1]

or a pharmaceutically acceptable salt or solvate thereof. In one aspect, the proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically and prophylactically effective amounts are from about 15 to 500 mg per day. In another aspect, the compound is administered at least one of continuously, intermittently, systemically, or locally. In another aspect, the deregulated FLT3 is defined further as a mutated FLT3 is constitutively active. In another aspect, the compound is administered orally, intravenously, or intraperitoneally. In another aspect, the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate. In another aspect, the FLT3 is at least one of FLT3-ITD or FLT3-TKD. In another aspect, the therapeutically or prophylactically effective amount of the compound is administered daily for as long as the subject is in need of treatment for the proliferative disease. In another aspect, the composition is provided at least one of sequentially or concomitantly, with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease subject, to maintain remission, or a relapsed/refractory proliferative disease subject. In another aspect, the compound is provided as a single agent or in combination with another pharmaceutical agent in a newly diagnosed proliferative disease pediatric subject, to maintain remission, or a relapsed/refractory proliferative disease pediatric subject. In another aspect, the subject is relapsed/refractory to prior FLT3 tyrosine kinase inhibition. In another aspect, the further comprises the step of determining if the subject is relapsed/refractory to a prior FLT3 tyrosine kinase inhibitor prior to providing the subject with treatment.

In another embodiment, the present invention includes a method for treating a subject with a proliferative disease comprising: administering to the subject in need of such treatment a therapeutically effective amount of Crenolanib or a salt thereof, wherein the cell proliferative disorder is characterized by deregulated FLT3 receptor tyrosine kinase activity, proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In one aspect, the compound is administered orally, intravenously, or intraperitoneally. In another aspect, the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate. In another aspect, the FLT3 is at least one of FLT3-ITD or FLT3-TKD. In another aspect, the Crenolanib is provided at least one of sequentially or concomitantly, with chemotherapy, radiotherapy, or surgery in a newly diagnosed proliferative disease, to maintain remission, or a relapsed/refractory proliferative disease. In another aspect, the Crenolanib is provided as a single agent or in combination with chemotherapy, radiotherapy or surgery for treatment of a pediatric subject with the proliferative disease. In another aspect, the Crenolanib is provided as a single agent to at least one of post standard induction therapy, or high dose induction therapy, in newly diagnosed proliferative disease. In another aspect, the Crenolanib is provided as a single agent in treatment of subjects with the proliferative disease that is either refractory to, or has relapsed after, standard or high dose chemotherapy, radiotherapy or surgery. In another aspect, the subject is relapsed/refractory to at least one other tyrosine kinase inhibitor, including but not limited to sorafenib, quizartinib, PLX3397, sunitinib, Midostaurin, or Lestaurtinib.

Yet another embodiment of the present invention includes a method for treating a subject suffering from leukemia comprising: obtaining a sample from the subject suspected of having a leukemia; determining from the subject sample that the subject has a deregulated FLT3 receptor tyrosine kinase; and administering to the subject in need of such treatment a therapeutically effective amount of Crenolanib or a salt thereof, wherein the leukemia is characterized by deregulated FLT3 receptor tyrosine kinase activity.

Another embodiment of the present invention includes a method for specifically inhibiting a deregulated receptor tyrosine kinase comprising: obtaining a subject sample and determining which receptor tyrosine kinases are deregulated; and administering to a mammal in need of such treatment a therapeutically effective amount of Crenolanib or a salt thereof, wherein the deregulated receptor tyrosine kinase is a FLT3 receptor tyrosine kinase. In one aspect, the proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the therapeutically and prophylactically effective amounts are from about 15 to 500 mg per day. In another aspect, the compound is administered at least one of continuously, intermittently, systemically, or locally. In another aspect, the deregulated FLT3 is defined further as a mutated FLT3 is constitutively active. In another aspect, the compound is administered orally, intravenously, or intraperitoneally. In another aspect, the Crenolanib is Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate. In another aspect, the FLT3 is at least one of FLT3-ITD or FLT3-TKD. In another aspect, the therapeutically or prophylactically effective amount of the compound is administered daily for as long as the subject is in need of treatment for the proliferative disease. In one aspect, the subject is provided treatment, one or more subject samples are obtained to determine the effect of the treatment, and treatment is continued until the proliferative disease is reduced or eliminated. In another aspect, the compound is provided at least one of sequentially or concomitantly, with another pharmaceutical agent in a newly diagnosed proliferative disease subject, to maintain remission of an existing subject, or a relapsed/refractory proliferative disease subject. In another aspect, the present invention is provided as a single agent or in combination with another pharmaceutical agent in a newly diagnosed proliferative disease subject, to maintain remission, or a relapsed/refractory proliferative disease subject. In another aspect, the present invention is provided as a single agent or in combination with another pharmaceutical agent in a newly diagnosed proliferative disease pediatric subject, to maintain remission, or a relapsed/refractory proliferative disease pediatric subject. In another aspect, the subject is relapsed/refractory to a prior FLT3 tyrosine kinase inhibitor.

Yet another embodiment of the present invention includes a method for treating a subject with cancer comprising: obtaining a sample suspected of having cancer from the subject; determining if the subject that has become resistant to prior FLT3 protein tyrosine kinase inhibition; and administering a therapeutically effective amount of Crenolanib or a salt thereof to overcome the resistance to the prior FLT3 protein tyrosine kinase inhibition.

The present invention provides methods of reducing or inhibiting the kinase activity of FLT3 in a cell or a subject, and the use of such methods for preventing or treating cell proliferative disorder(s) related to FLT3. Other features and advantages of the invention will be apparent from the following detailed description of the invention and from the claims.

BRIEF DESCRIPTION OF THE DRAWINGS

For a more complete understanding of the features and advantages of the present invention, reference is now made to the detailed description of the invention along with the accompanying figure in which:

(FIG. 1A): shows replicates of a first (left) and a second (right) standard dose-response curve for non-phosphorylated ABL1; (FIG. 1B): shows replicates of a first (left) and a second (right) standard dose-response curve for phosphorylated ABL1; (FIG. 1C): shows replicates of a first (left) and a second (right) standard dose-response curve for non-phosphorylated ABL(T315I); (FIG. 1D): shows replicates of a first (left) and a second (right) standard dose-response curve for phosphorylated ABL (T315I). The amount of kinase measured by qPCR (signal; y-axis) is plotted against the corresponding crenolanib concentration in nanomolar in log 10 scale (x-axis). Data points marked with an "x" were not used for Kd determination.

(FIG. 2A): shows replicates of a first (left) and a second (right) standard dose-response curves for non-autoinhibited state of FLT3; (FIG. 2B): shows replicates of a first (left) and a second (right) standard dose-response curves for autoinhibited state of FLT3. The amount of kinase measured by qPCR (signal; y-axis) is plotted against the corresponding crenolanib concentration in nanomolar in log 10 scale (x-axis). Data points marked with an "x" were not used for Kd determination.

DETAILED DESCRIPTION OF THE INVENTION

Figure 1A:
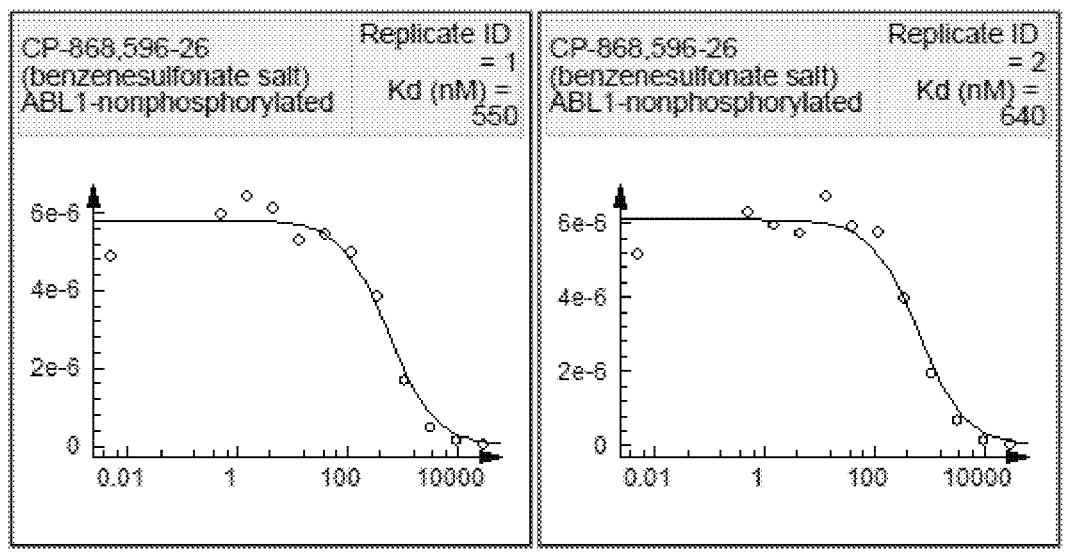
FIGS. 1A to 1D show the affinity of the besylate salt of the present invention for the non-phosphorylated and phosphorylated states of ABL1 and ABL (T315I)
Figure 1B:
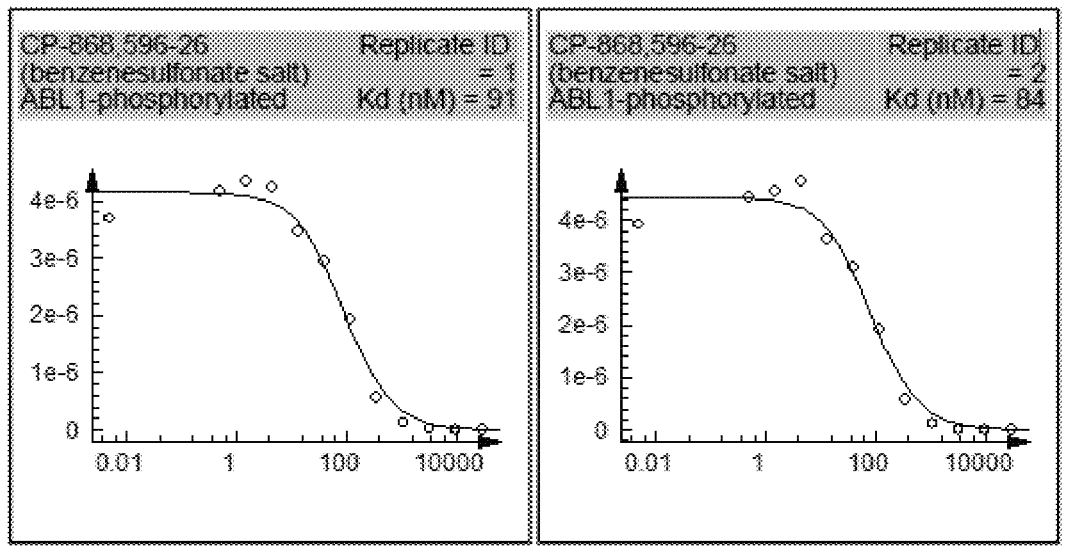
Figure 1C:
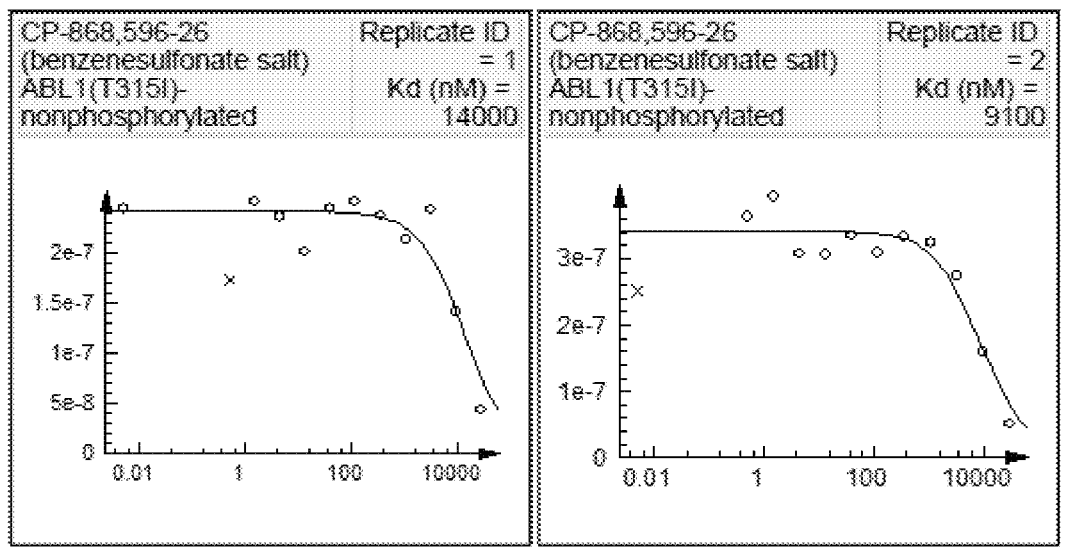
Figure 1D:
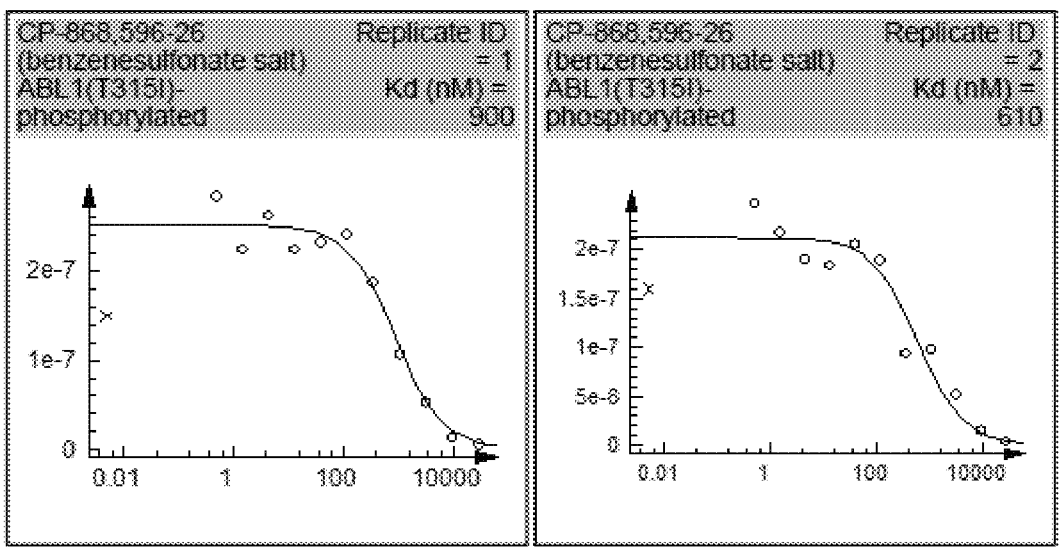

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention comprises the use of the compounds of the present invention to inhibit FLT3 kinase activity in a cell or a subject, or to treat disorders related to FLT3 kinase activity or expression in a subject.

In one embodiment to this aspect, the present invention provides a method for reducing or inhibiting the kinase activity of FLT3 in a cell comprising the step of contacting the cell with a compound of the present invention. The present invention also provides a method for reducing or inhibiting the kinase activity of FLT3 in a subject comprising the step of administering a compound of the present invention to the subject. The present invention further provides a method of inhibiting cell proliferation in a cell comprising the step of contacting the cell with a compound of the present invention.

The term "subject" refers to an animal, such as a mammal or a human, who has been the object of treatment, observation or experiment.

The term "contacting" refers to the addition of the present invention or pharmaceutically acceptable salt to cells such that the compound is taken up by the cell.

In other embodiments to this aspect, the present invention provides both prophylactic and therapeutic methods for treating a subject at risk or susceptible to developing a cell proliferative disorder driven by aberrant kinase activity of FLT3. In one example, the invention provides methods for preventing a cell proliferative disorder related to FLT3, comprising administration of a prophylactically effective amount of a pharmaceutical composition comprising a compound of the present invention in a subject. Administration of said prophylactic agent can occur prior to the manifestation of symptoms characteristic of the FLT3 driven cell proliferative disorder, such that a disease or disorder is prevented or, alternatively, delayed in its progression.

The term "prophylactically effective amount" refers to an amount of active compound or pharmaceutical salt that inhibits or delays in a subject the onset of a disorder as being sought by a researcher, veterinarian, medical doctor or other clinician.

The term "therapeutically effective amount" as used herein, refers to an amount of active compound or pharmaceutical salt that elicits the biological or medicinal response in a subject that is being sought by a researcher, veterinarian, medical doctor or other clinician, which includes alleviation of the symptoms of the disease or disorder being treated.

Methods for determining therapeutically and prophylactically effective doses for pharmaceutical compositions comprising a compound of the present invention are known in the art.

As used herein, the term "composition" is intended to encompass a product comprising the specified ingredients in the specified amounts, as well as any product which results, directly or indirectly, from combinations of the specified ingredients in the specified amounts.

As used herein, the terms "disorder related to FLT3," or "disorders related to FLT3 receptor," or "disorders related to FLT3 receptor tyrosine kinase," or "FLT3 driven cell proliferative disorder" includes diseases associated with or implicating FLT3 activity, for example, mutations leading to constitutive activation of FLT3. Examples of "disorders related to FLT3" include disorders resulting from over stimulation of FLT3 due to mutations in FLT3, or disorders resulting from abnormally high amount of FLT3 activity due to abnormally high amount of mutations in FLT3. It is known that overactivity of FLT3 has been implicated in the pathogenesis of many diseases, including the following listed cell proliferative disorders, neoplastic disorders and cancers.

The term "cell proliferative disorders" refers to excess cell proliferation of one or more subset of cells in a multicellular organism resulting in harm (i.e. discomfort or decreased life expectancy) to the multicellular organism. Cell proliferative disorders can occur in different types of animals and humans. As used herein, "cell proliferative disorders" include neoplastic disorders.

The term "neoplastic disorder' as used herein, refers to a tumor resulting from abnormal or uncontrolled cellular growth. Examples of neoplastic disorders include, but are not limited to the following disorders, for instance: the myeloproliferative disorders, such as thrombocytopenia, essential thrombocytosis (ET), agnogenic myeloid metaplasia, myelofibrosis (MF), myelofibrosis with myeloid metaplasia (MMM), chronic idiopathic myelofibrosis (UIMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematological malignancies, including myelodysplasia, multiple myeloma, leukemias, and lymphomas. Examples of hematological malignancies include, for instance, leukemias, lymphomas, Hodgkin's disease, and myeloma. Also, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), myelodysplastic syndromes (MDSs), myeloproliferative disorders (MPD), and multiple myeloma (MM).

In a further embodiment, the present invention can be combined with another therapy as a combination therapy for treating or inhibiting the onset of a cell proliferative disorder related to FLT3 in a subject. The combination therapy comprises the administration of a prophylactically and therapeutically effective amount of a compound of the present invention and one or more other anti-cell proliferation therapies including, but not limited to, chemotherapy and radiation therapy.

In an embodiment of the present invention, a compound of the present invention may be administered in combination with chemotherapy. Used herein, chemotherapy refers to a therapy involving a chemotherapeutic agent. A variety of chemotherapeutic agents may be used in combination with the present invention. By way of example only, taxane compounds, specifically docetaxel, is safely administered in combination with a compound of the present invention in a dosage of 75 mg per square meter (mg/m²) of body surface area.

Chemotherapy is known to those skilled in the art. The appropriate dosage and scheme for chemotherapy will be similar to those already employed in clinical therapies wherein the chemotherapy is delivered in combination with other therapies or used alone.

In another embodiment of the present invention, compounds of the present invention may be administered in combination with radiation therapy. Used herein, "radiation therapy" refers to a therapy that comprises the exposure of a subject in need to radiation. Radiation therapy is known to those skilled in the art. The appropriate dosage and scheme for radiation therapy will be similar to those already employed in clinical therapies wherein the radiation therapy is delivered in combination with other therapies or used alone.

In another embodiment of the present invention, the compounds of the present invention may be administered in combination with a targeted therapy. As used herein, "targeted therapy" refers to a therapy targeting a particular class of proteins involved in tumor development or oncogenic signaling. For example, tyrosine kinase inhibitors against vascular endothelial growth factor have been used in treating cancers.

The present invention also includes methods that include the use of a second pharmaceutical agent in addition to compounds of the present invention, the two may be administered simultaneously or sequentially (in either order).

In one embodiment, the present invention therapeutically effective amounts of the compound having formula I:

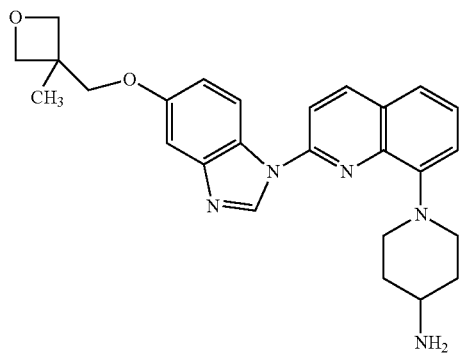 [SMILES: CC1(COc2ccc3c(c2)ncn3-c2ccc3cccc(N4CCC(N)CC4)c3n2)COC1]

or a pharmaceutically acceptable salt or solvate thereof, in a therapeutically or prophylactically effective amount against a proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. Pharmaceutically acceptable salts including hydrochloride, phosphate and lactate are prepared in a manner similar to the benzenesulfonate salt and are well known to those of moderate skill in the art.

Compounds of the present invention may be administered to a subject systemically, for example, orally, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 15 to 500, 25 to 450, 50 to 400, 100 to 350, 150 to 300, 200 to 250, 15, 25, 50, 75, 100, 150, 200, 250, 300, 400, 450, or 500 mg per day. The compounds of the present invention may be administered on a daily regimen, once, twice, three or more times per day. Optimal doses to be administered may be determined by those skilled in the art, and will vary with the compound of the present invention used, the mode of administration, the time of administration, the strength of the preparation, the details of the disease condition. One or more factors associated with subject characteristics, such as age, weight, and diet will call for dosage adjustments. Techniques and compositions for making useful dosage forms using the Crenolanib are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); relevant portions incorporated herein by reference.

A dosage unit for use of Crenolanib, may be a single compound or mixtures thereof with other compounds, e.g., a potentiator. The compounds may be mixed together, form ionic or even covalent bonds. The compounds of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the compounds of the present invention to a patient in need of therapy that includes the compound of Formula I.

The Crenolanib is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the Crenolanib may be formulated to provide, e.g., maximum and/or consistent dosing for the particular form for oral, rectal, topical, intravenous injection or parenteral administration. While the Crenolanib may be administered alone, it will generally be provided in a stable salt form mixed with a pharmaceutically acceptable carrier. The carrier may be solid or liquid, depending on the type and/or location of administration selected.

Preparation of the compounds of the present invention. General synthetic methods which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application Publication No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention, including Crenolanib as Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate.

Biological Activity.

In Vitro Assays. The following representative in vitro assays were performed in determining the FLT3 biological activity of the present invention. These are given to illustrate the invention in a non-limiting fashion.

Inhibition of wild type and mutated FLT3 enzyme activity and specificity for the inhibition of the phosphorylated form of FLT3 exemplify the specific inhibition of the FLT3 enzyme and cellular processes that are dependent on FLT3 activity. All of the examples herein show significant and specific inhibition of the FLT3 kinase and FLT3-dependent cellular responses.

Competitive binding assay. Inhibition of the kinase domain of the human FLT3 receptor was performed using the KINOMEscan KdElect assay protocol. The KINOMEscan platform utilizes a high-throughput competitive binding technology. The assay was performed by combining DNA-tagged kinase, immobilized ligand, and the present invention. The ability of the present invention to compete with immobilized ligand was measured using quantitative PCR of the DNA tag. The competition binding assay was used to evaluate the present invention against a panel of 96 human protein kinases.

Kinase-tagged T7 phage strains were grown in parallel in 24-well blocks in an *E. coli* host derived from the BL21 strain. *E. coli* were grown to log phase and infected with T7 phage from a frozen stock and incubated with shaking at 32 degrees Celsius until lysis. The lysates were then centrifuged and filtered. The remaining kinases were produced in HEK-293 cells and tagged with DNA for quantitative PCR detection. Affinity resins for the kinase assay were generated by treating streptavidin-coated magnetic beads with biotinylated small molecule ligands for 30 minutes at room temperature. The liganded beads were blocked with excess biotin and washed with blocking buffer consisting of Sea Block, 1% Bovine Serum Albumin (BSA) 0.05% Tween 20, 1 mM Dithithreitol (DTT) in order to reduce non-specific phage binding. An 11-point 3-fold serial dilution of the present invention was prepared as a 40× stock in 100% Dimethyl sulfoxide (DMSO) and diluted to 1× directly into the assay.

Binding reactions were initiated by combining the liganded affinity beads, kinases, and the present invention in 1× binding buffer consisting of 20% Sea Block, 0.17 Phosphate Buffered Saline (PBS), 0.05% Tween 20, 6 mM DTT. All reactions were performed in polypropylene 384-well plates in a final volume of 0.04 mL. The plates were incubated for 1 hour while shaking at room temperature. The affinity beads were washed with 1×PBS and 0.05% Tween 20 buffer, then re-suspended in elution buffer consisting of 1×PBS, 0.05% Tween 20, 0.5 uM non-biotinylated affinity ligand. Following re-suspension, the affinity beads were incubated at room temperature with shaking. The elutant kinase concentration was then measured by quantitative PCR.

Binding constants (Kds) were calculated with a standard dose-response curve using the Hill equation. Curves were fitted using a non-linear least square fit with the Levenberg-Marquardt algorithm. Kds of the present invention were compared to both a negative DMSO control and a positive control compound. The binding affinity of the present invention was visualized using the compound profile visualization interaction map, TREEspot.

Direct enzyme phosphorylation assay. The Millipore Kinase IC50 Profiler assay was used to screen the present invention against a panel of normal FLT3 and mutated FLT3 kinases. For assays of both kinases, the FLT3 enzyme was incubated with 8 mM of 3-(N-morpholino)propanesulfonic acid (MOPS) at a pH of 7.0, 0.2 mM Ethylenediaminetetraacetic acid (EDTA), 50 uM, a synthetic Abl peptide substrate EAIYAAPFAKKK, 10 mM MgAcetate and [$\gamma$-$^{33}$P-ATP]. The reaction was initiated by the addition of MgATp mix. The reaction mixture was incubated for 40 minutes at room temperature and halted by the addition of 3% phosphoric acid solution. 10 uL of the reaction solution was spotted on P30 filtermat and washed three times in 75 mM phosphoric acid for 5 minutes and then once in methanol prior to drying and scintillation counting. The scintillation values for each replicate, including positive and negative controls, were analyzed using XLFit version 5.1 to determine the IC50 values for the present invention against normal and mutated FLT3.

Biological Data for Phosphorylated Kinase Affinity.

Analysis of the affinity of the besylate salt of the present invention for phosphorylated and non-phosphorylated kinases, ABL1 and ABL(T315I), demonstrates that crenolanib besylate exhibits the characteristic mechanism of a type I inhibitor (FIGS. 1A to 1D). The binding constants for phosphorylated ABL1 (Kd=88 nM) and ABL(T315I) (Kd=760 nM) for the present invention were 7 and 15-fold lower than its binding constants for non-phosphorylated ABL1 (Kd=600 nM) and ABL(T315I) (Kd=12000 nM), respectively (Table 1). Though the present invention is not active against ABL, the besylate salt of the invention has significantly greater affinity for the phosphorylated kinase which suggests that crenolanib is a type I TKI.

TABLE 1

Crenolanib besylate is a type I TKI with increased affinity for phosphorylated kinases.

| Kinase Target | Crenolanib Besylate Kd |
|---|---|
| ABL1(T315I) nonphosphorylated | 12000 nM |
| ABL1(T315I) phosphorylated | 760 nM |
| ABL1-nonphosphorylated | 600 nM |
| ABL1-phosphorylated | 88 nM |

Figure 2A:
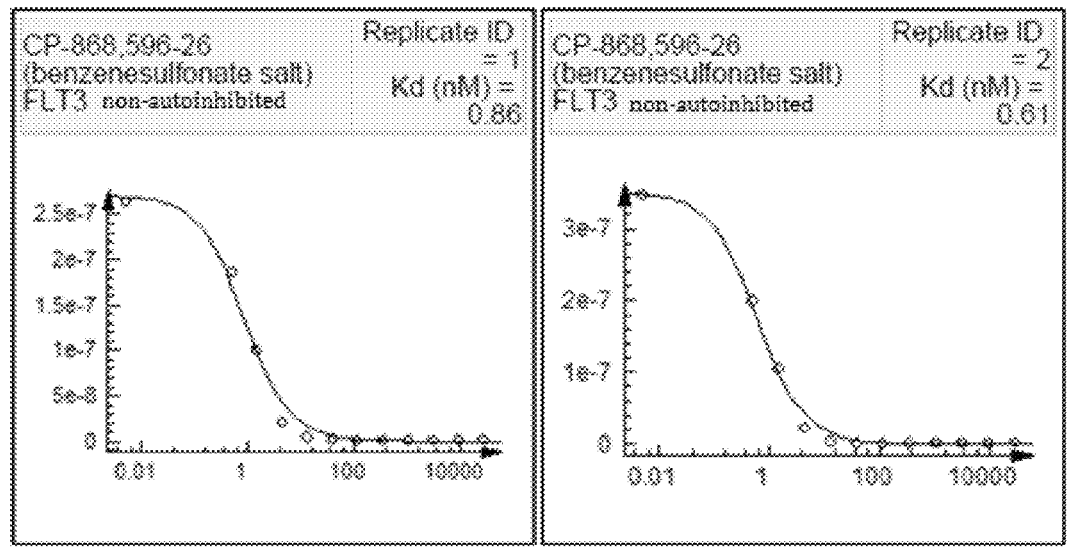
FIGS. 2A and 2B show the affinity of the besylate salt of the present invention for the non-autoinhibited and autoinhibited states of FLT3.
Figure 2B:
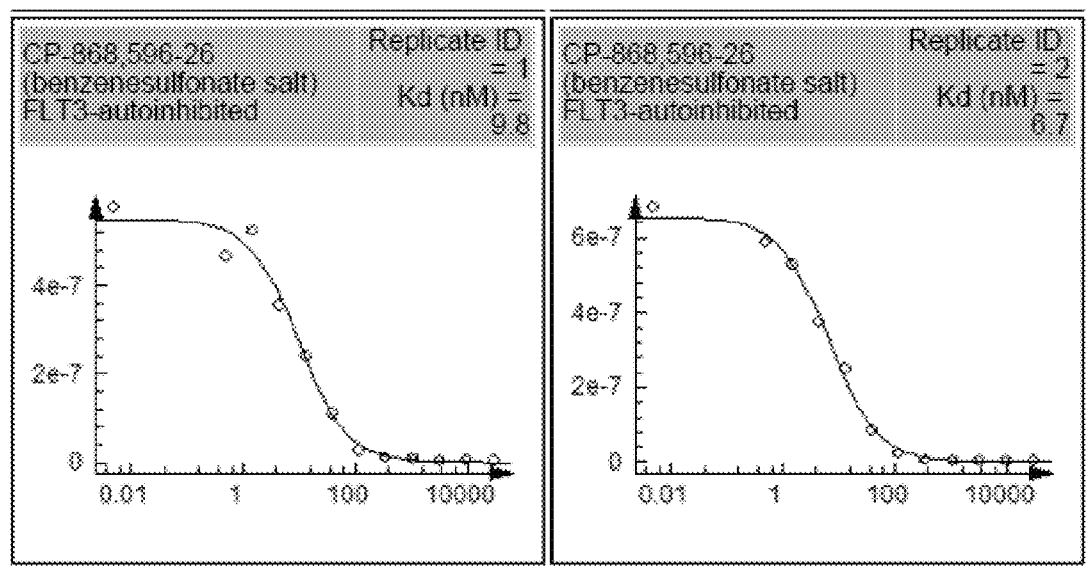

The difference in binding affinities of the besylate salt of the present invention for the non-autoinhibited and autoinhibited states of FLT3 also indicate that the molecule functions as a type I inhibitor. As shown in FIGS. 2A and 2B and Table 2, the besylate salt of the present invention has a Kd value of 0.61 nM for non-autoinhibited FLT3 and a Kd value of 6.7 nM for autoinhibited FLT3. The besylate salt of the present invention thus has an approximately 10-fold affinity shift between the non-autoinhibited and autoinhibited states of FLT3. This value is within the range of affinity shifts reported for other type I tyrosine kinase inhibitors and is far outside the range of 100- to 1000-fold affinity shifts reported for type II TKIs. See Davis, M I et al., Comprehensive analysis of kinase inhibitor selectivity. Nat. Biotechnology. 2011; 29 (10): 1046-1051; Zhang, J et al., Targeting cancer with small molecule kinase inhibitors. Nat Rev Cancer. 2009; 9(1): 28-39; Liu, Y et al., Rational design of inhibitors that bind to inactive kinase conformations. Nat Chem. Biol. 2006; 2(7): 358-364.

TABLE 2

Crenolanib besylate is a type I TKI with increased affinity for phosphorylated FLT3.

| Kinase Target | Crenolanib Besylate Kd |
|---|---|
| FLT3 phosphorylated | 0.61 nM |
| FLT3 nonphosphorylated | 6.7 nM |

Biological Data for Wild Type FLT3.

Crenolanib besylate has demonstrated activity as a specific and potent inhibitor of class III receptor RTKs. TheKd of crenolanib against the wild-type receptors FLT3, PDGFRB, and PDGFRA, PDGFRB, and FLT3 is 0.74 nM, 2.1 nM, and 3.2 nM, respectively (Table 3).

TABLE 3

Specificity of the besylate salt of the present invention for class III receptor tyrosine kinases including FLT3, PDGFRA, and PDGFRB.

| RTK | Binding Constant (Kd) |
|---|---|
| FLT3 wild type | 0.74 nM |
| PDGFRB wild type | 2.1 nM |
| PDGFRA wild type | 3.2 nM |

Crenolanib besylate does not inhibit any other known RTKs (e.g. VEGFR, FGFR) or other serine/threonine kinases (e.g. Abl, Raf) at clinically achievable concentrations. Crenolanib besylate is 300- to >5000-fold selective relative to concentrations required to inhibit other angiogenic kinases, VEGFR-2, FGFR-2, and TIE-2 (Table 4). Crenolanib besylate is >100-fold selective relative to concentrations required to inhibit a variety of other kinases involved in the angiogenesis cascade, such as VEGFR, FGFR as well as other kinases like EGFR, erbB2, src etc.

TABLE 4

Lack of inhibition of the besylate salt of the present invention for other RTKs known in the art.

| RTK | IC50 (ng/mL) |
| --- | --- |
| VEGFR-2 | 121 |
| FGFR-2 | >2250 |
| TIE-2 | >2250 |
| Src | 2208 |
| EGFR | >4435 |
| erbB2 | >4435 |

The affinity of the besylate salt of the present invention for wild type FLT3 is presented in Table 5. All binding constants are presented in nanomolar concentration. The binding affinity (Kd) of the besylate salt of the present invention for wild type FLT3 is 0.74 nM. The affinity of the besylate salt of the present invention is the highest for wild type FLT3 when compared to a number of other FLT3 TKIs inhibitors known in the art.

TABLE 5

Binding constants (Kd) of the besylate salt of the present invention compared to other FLT3 TKIs known in the art for wild type FLT3.

| RTK | Compound | Binding Constant (Kd) |
| --- | --- | --- |
| FLT3 wild type | Crenolanib Besylate | 0.74M |
| | AST-487 | 0.79M |
| | Quizartinib/AC220 | 1.3 nM |
| | Tandutinib/MLN-518 | 3 nM |
| | Lestaurtinib/CEP-701 | 8.5 nM |
| | Midostaurin/PKC-412 | 13 nM |

Figure 3:
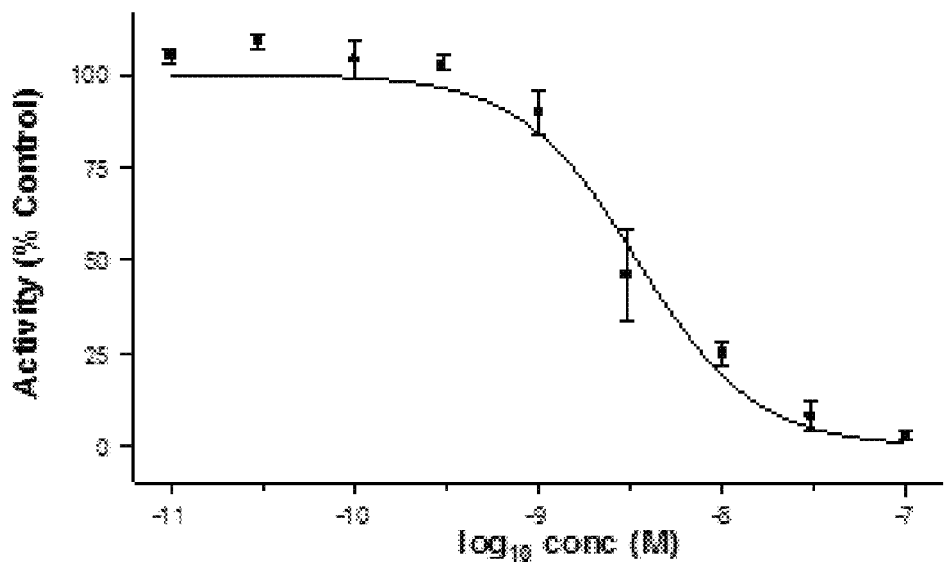
FIG. 3 shows the dose-response curve (n=2) for IC50 determination of the besylate salt of the present invention for wild-type FLT3. The activity of the besylate salt of crenolanib is plotted against the corresponding molar concentration in log 10 scale.

The activity of the besylate salt of the present invention for FLT3 wild type was determined using a direct enzymatic Millipore IC50 profiler assay. In the direct enzymatic measurement assay, the IC50 of the besylate salt of the current invention against wild type FLT3 was 3 nM (FIG. 3 and Table 6).

TABLE 6

Potency of the besylate salt of the present invention against FLT3 wild type as measured by direct enzymatic phosphorylation

| RTK | Compound | IC50 |
| --- | --- | --- |
| FLT3 wild type | Crenolanib Besylate | 3 nM |

Biological Data for the FLT3-ITD Mutation.

Figure 4:
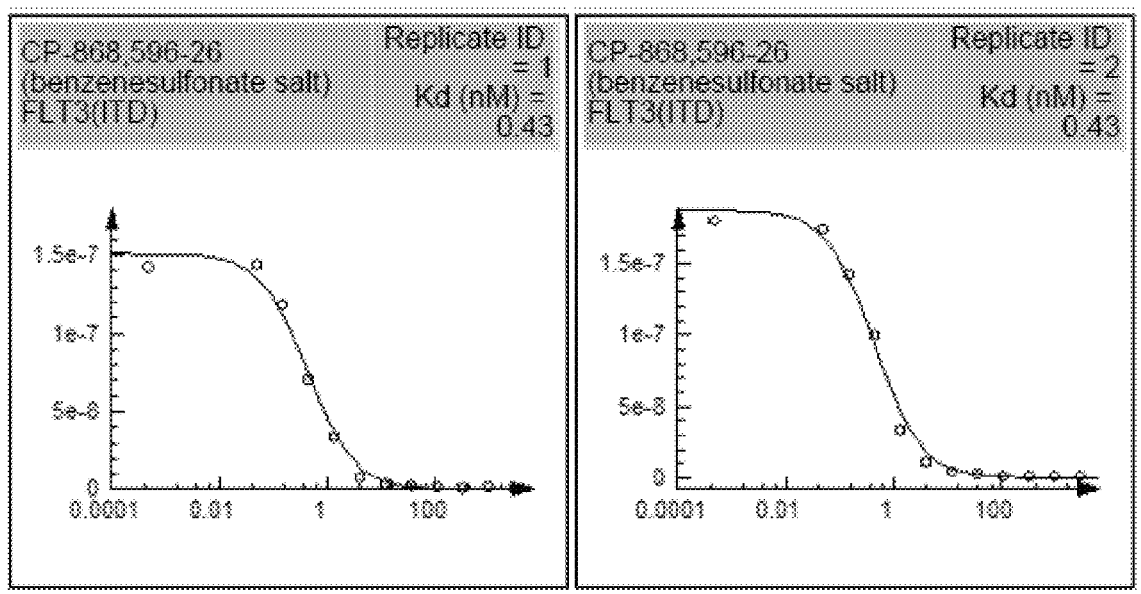
FIG. 4 shows replicates of a first (left) and a second (right) standard dose-response curves for Kd determination of the besylate salt of the present invention for FLT3 ITD. The amount of kinase measured by qPCR (signal; y-axis) is plotted against the corresponding crenolanib concentration in nanomolar in log 10 scale (x-axis).

The affinity of the besylate salt of the present invention for FLT3 with an ITD mutation is presented in Table 8. All binding constants are presented in nanomolar concentration. The Kd of the besylate salt of the present invention for FLT3-ITD is 0.43 Nm (FIG. 4). The affinity of the besylate salt of the present invention is the highest for mutant FLT3-ITD when compared to a number of other FLT3 TKIs inhibitors known in the art. A portion of this data and the basic techniques for measuring the affinities were published by the present inventors, see Muralidhara C, Ramachandran A, Jain V. Crenolanib, a novel type I, mutant-specific inhibitor of class III receptor tyrosine kinases, preferentially binds to phosphorylated kinases. Cancer Research. 2012; 72 (8 Supplement): 3683.

TABLE 8

Binding constants (Kd) of the besylate salt of the present invention compared to other FLT3 TKIs known in the art for FLT3-ITD.

| RTK | Compound | Binding Constant (Kd) |
| --- | --- | --- |
| FLT3 ITD | Crenolanib besylate | 0.43 nM |
| | Sunitinib | 0.99 nM |
| | Lestaurtinib/CEP-701 | 1.5 nM |
| | Quizartinib/AC220 | 8.8 nM |
| | Tandutinib/MLN-518 | 9.1 nM |
| | Midostaurin/PKC-412 | 11 nM |
| | AST-487 | 11 nM |
| | Sorafenib | 79 nM |

Biological Data for the FLT3-D835 Mutation.

Figure 5A:
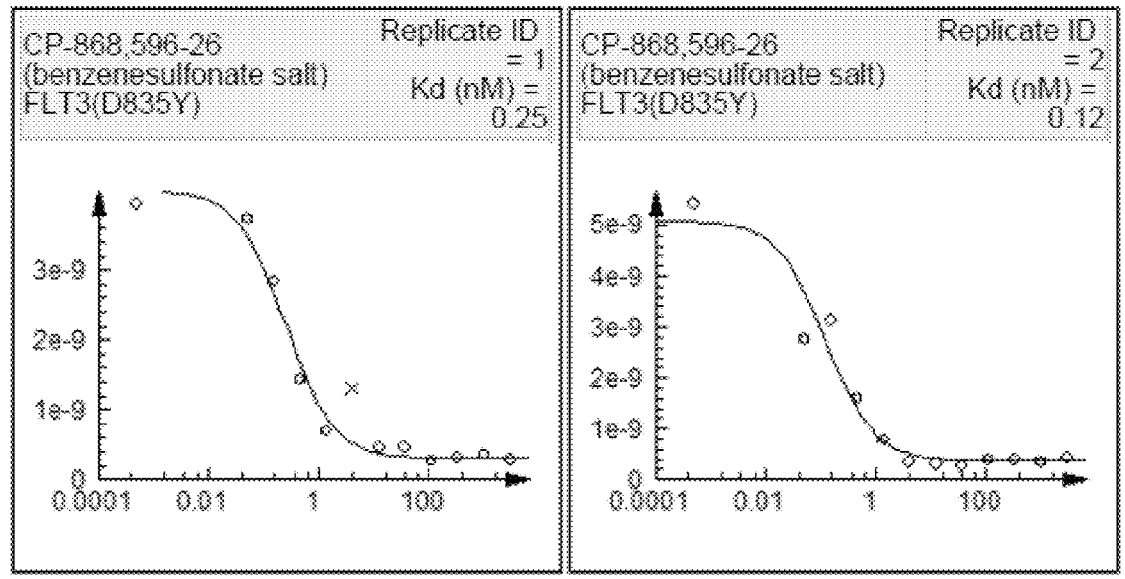
FIGS. 5A and 5B show the replicates of standard dose-response curves for Kd determination of the besylate salt of the present invention for (FIG. 5A) replicates of a first (left) and a second (right) for FLT3 D835Y and (FIG. 5B) replicates of a first (left) and a second (right) FLT3 D835H. The amount of kinase measured by qPCR (signal; y-axis) is plotted against the corresponding crenolanib concentration in nanomolar in log 10 scale (x-axis). Data points marked with an "x" were not used for Kd determination.
Figure 5B:
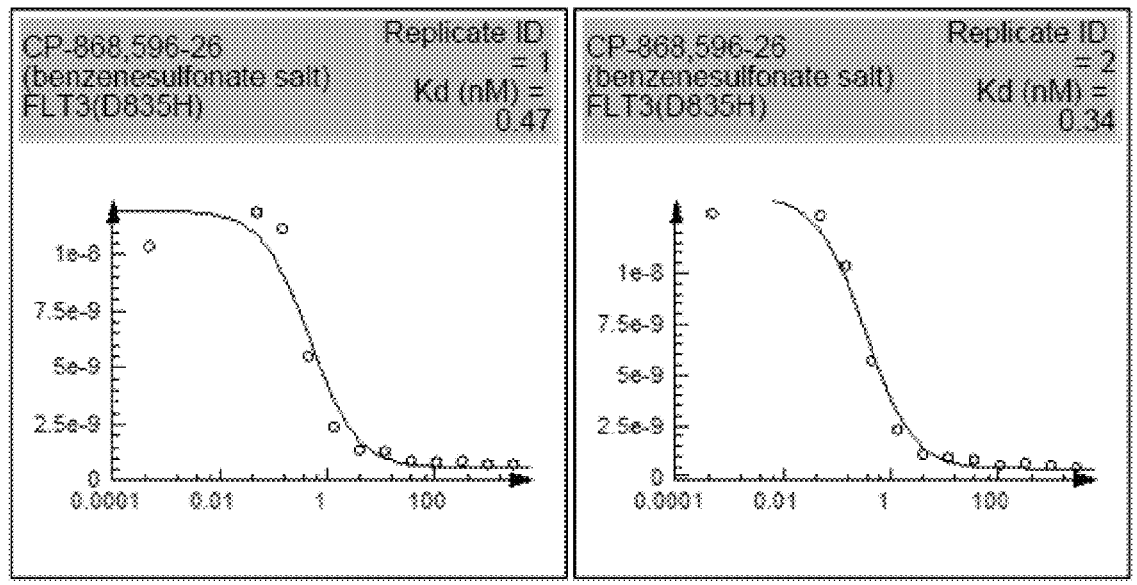

The activity of the besylate salt of the present invention against FLT3 tyrosine kinase domain mutations D835Y and D835H is compared against other inhibitors known in the art (Table 11). All binding constants are presented in nanomolar concentration. The Kd of the besylate salt of the present invention for the FLT3 D835Y and D835H mutations is 0.18 nM and 0.26 nM, respectively (FIGS. 5A and 5B, respectively). The affinity of the besylate salt of the present invention is the highest for FLT3 D835Y and FLT3 D835H mutations when compared to a number of other FLT3 TKIs inhibitors known in the art. See Muralidhara C, Ramachandran A, Jain V. Crenolanib, a novel type I, mutant-specific inhibitor of class III receptor tyrosine kinases, preferentially binds to phosphorylated kinases. Cancer Research. 2012; 72 (8 Supplement): 3683, by the present inventors.

TABLE 11

Binding constants (Kd) of the besylate salt of the present invention compared to other FLT3 TKIs known in the art for FLT3 D835Y and FLT3 D835H.

| | | Binding Constant (Kd) | |
| --- | --- | --- | --- |
| RTK | Compound | FLT3 D835Y | FLT3 D835H |
| FLT3 D835 | Crenolanib Besylate | 0.18 nM | 0.4 nM |
| | Lestaurtinib | 0.57 nM | 0.66 nM |
| | Sunitinib | 2.3 nM | 4.3 nM |
| | AC220 | 7.1 nM | 3.7 nM |
| | AST-487 | 11 nM | 4.9 nM |
| | PKC-412 | 15 nM | 6.8 nM |
| | Sorafenib | 82 nM | 30 nM |

Figure 6:
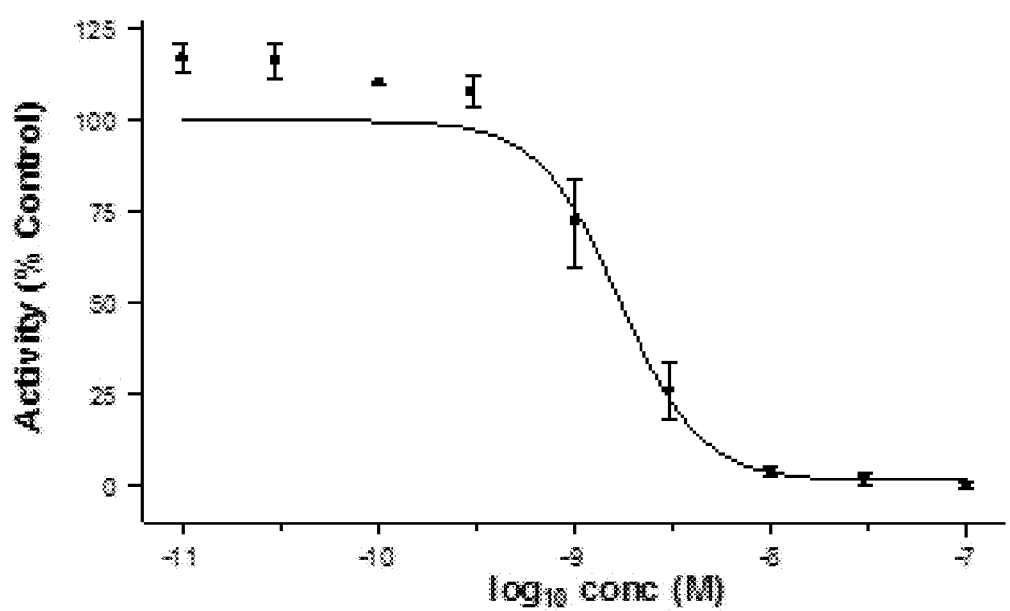
FIG. 6 shows the dose-response curve (n=2) for IC50 determination of the besylate salt of the present invention for FLT3 D835Y. The activity of the besylate salt of crenolanib is plotted against the corresponding molar concentration in log 10 scale.

The activity of the besylate salt of the present invention was determined using a direct enzymatic Millipore IC50 profiler assay (Table 12). All IC50 values are presented in nanomolar concentration. In the direct enzymatic measurement assay, the IC50 of the besylate salt of the current invention against the FLT3 TKD mutation D835Y was 2 nM (FIG. 6).

TABLE 12

Potency of the besylate salt of the present invention against FLT3 D835Y as measured by direct enzymatic phosphorylation.

| RTK | Compound | Binding Affinity (Kd) |
| --- | --- | --- |
| FLT3 D835Y | Crenolanib Besylate | 2 nM |

Additional biological data supporting the present invention was published by investigators from two academic centers working in collaboration with the present inventors. Briefly, the supporting data pertains to the biological activity of the besylate salt of the present invention for FLT3 wildtype, FLT3-ITD mutation, FLT3 D835 mutation, dual FLT3-ITD/

FLT3-D835 mutation, Type I FLT3 TKI crenolanib besylate overcoming resistance associated with a Type II FLT3TKI, and combining the besylate salt of the present invention with cytotoxic chemotherapy. See Galanis A, Rajkhowa T, Muralidhara C, et al. Crenolanib: A next generation FLT3 inhibitor. Cancer Research. 2012; 72(8 Supplement): 3660; See Galanis A, Rajkhowa T, Ramachandran A, et al. Crenolanib is a highly potent, selective, FLT3 TKI with activity against D835 mutations. Blood. 2012; 120: 1341; See Zimmerman E, Hu S, Li L, et al. Evaluation of crenolanib (CP-868,596) for the treatment of FLT3-ITD positive AML. European Journal of Cancer. 2012; 48 (Supplement 6): 38.

Biological Data for Wild Type FLT3.

The potency of the besylate salt of the present invention for FLT3 wild type was determined in the FLT3 wild type specific cell line SEMK2 (Table 7). Crenolanib besylate inhibited the phosphorylation of the wild type FLT3 receptor in SEMK2 cells at a nanomolar IC50 concentration of 2.2 nM. See Galanis A, Rajkhowa T, Muralidhara C, et al. Crenolanib: A next generation FLT3 inhibitor. Cancer Research. 2012; 72(8 Supplement): 3660.

Crenolanib besylate inhibition of phosphorylation of the wild type receptor was evaluated in the wild type cell line HL60. The inhibition levels of crenolanib besylate against the wild type FLT3 receptor cell line was compared to the potency of another FLT3 inhibitor in the art, sorafenib. Crenolanib besylate and sorafenib exhibit increased phosphorylation inhibition in a dose dependent fashion. Crenolanib besylate is a more potent inhibitor of FLT3 wild type phosphorylation than sorafenib. See Galanis A, Rajkhowa T, Muralidhara C, et al. Crenolanib: A next generation FLT3 inhibitor. Cancer Research. 2012; 72(8 Supplement): 3660.

Biological Data for the FLT3-ITD Mutation.

The ability of the besylate salt of the present invention to inhibit phosphorylated FLT3 in cell lines expressing FLT3 ITD, including MV-411, Molm 14, and Molm 13, was examined by western blot. Crenolanib besylate inhibited the phosphorylation of the FLT3-ITD receptor in the cell lines at nanomolar IC50 concentrations of 1.28 nM 2.65 nM, and 4.9 nM, respectively (Table 9). See Galanis A, Rajkhowa T, Muralidhara C, et al. Crenolanib: A next generation FLT3 inhibitor. Cancer Research. 2012; 72(8 Supplement): 3660.

TABLE 9

Potency of the besylate salt of the present invention against FLT3 ITD as measured by phosphorylation inhibition in FLT3 ITD cell lines MV-411, Molm 14, and Molm 13.

| RTK | Cell Line | IC50 |
| --- | --- | --- |
| FLT3-ITD | MV-411 | 1.28 nM |
|  | Molm 14 | 2.65 |
|  | Molm 13 | 4.9 nM |

The ability of crenolanib besylate to induce apoptosis in FLT3 ITD expressing Molm 14 cells was compared to that of sorafenib, another FLT3 inhibitor known in the art, via an Annexin V/Propidium iodide staining assay. The cytotoxic response of the Molm 14 cells to crenolanib besylate was significantly higher as compared to sorafenib (Table 10) at concentrations 20 nM to 100 nM. See Galanis A, Rajkhowa T, Ramachandran A, et al. Crenolanib is a highly potent, selective, FLT3 TKI with activity against D835 mutations. Blood. 2012; 120: 1341.

TABLE 10

Crenolanib besylate induces significantly greater apoptosis in FLT3 ITD expressing cell line Molm 14 than sorafenib, another FLT3 inhibitor known in the art.

|  | Percent Apoptosis | |
| --- | --- | --- |
| Compound Concentration | Crenolanib | Sorafenib |
| 20 nM | 32.79% | 13.07% |
| 50 nM | 44.99% | 30.21% |
| 100 nM | 51.17% | 44.09% |

The ability of crenolanib besylate to inhibit FLT3 ITD signalling in primary AML patient blast samples was determined via MTT assay. Samples from five patients harboring the FLT3 ITD mutation were treated with increasing concentrations of crenolanib besylate. Cytotoxicity was observed in a dose dependent fashion. See Galanis A, Rajkhowa T, Muralidhara C, et al. Crenolanib: A next generation FLT3 inhibitor. Cancer Research. 2012; 72(8 Supplement): 3660.

The in vivo anti-leukemic effect of crenolanib besylate was determined using a MV-411FLT3-ITD positive AML xenograft mouse model. Ten days after tail vein injection of luciferase-expressing MV-411 cells, crenolanib besylate or vehicle was administered at a dose of 15 mg/kg intraperitoneally to male NSG mice twice daily for two days followed by once daily for 2 days. As depicted in, crenolanib treatment significantly suppressed MV-4,1-luciferase bone marrow infiltration compared to vehicle treated animals ($p<0.01$). See Zimmerman E, Hu S, Li L, et al. Evaluation of crenolanib (CP-868,596) for the treatment of FLT3-ITD positive AML. European Journal of Cancer. 2012; 48 (Supplement 6): 386.

Biological Data for the FLT3-D835 Mutation.

The activity of crenolanib besylate was tested against Ba/F3 cells with D835Y and D835N mutations. Crenolanib potently decreased the viability of Ba/F3 expressing D835Y and D835N, with IC50 values of 6.38 and 3.93 nM, respectively (Table 13). The sensitivity of crenolanib besylate was superior to that of AC220 treatment for Ba/F3 D835Y and similar for Ba/F3 D835N.

TABLE 13

Potency of the besylate salt of the present invention compared to AC220, another FLT3 TKI known in the art, against FLT3 D835Y and FLT3 D835N.

| Cell line | Crenolanib IC50 pFLT3 | AC220 IC50 pFLT3 |
| --- | --- | --- |
| Ba/F3 D835Y | 6.38 nM | 26.3 nM |
| Ba/F3 D835N | 3.93 nM | 2.36 nM |

The ability of crenolanib besylate to inhibit FLT3 D835V signaling in a primary AML patient blast sample was determined via western blot and MTT assay. The sample was taken from a 77 year old male with a chronic myeloproliferative disease that developed AML. The AML cells were noted to have a FLT3 D835 mutation. Western blot analysis of the patient blats incubated in vitro with crenolanid showed inhibition with n IC50 of 2 nM. Sorafenib, another FLT3 inhibitor known in the art, at 20 nM was ineffective at inhibiting FLT3 in the blast cells. The blasts showed a greater cytotoxic response to crenolanib compared with sorafenib in an MTT assay following 3 day exposure. See Galanis A, Rajkhowa T, Ramachandran A, et al. Crenolanib is a highly potent, selective, FLT3 TKI with activity against D835 mutations. Blood. 2012; 120: 1341.

Biological Data for FLT3-ITD/FLT3-D835 Mutation.

The activity of crenolanib besylate was tested against Ba/F3 cells with a double FLT3 D835Y and FLT3 ITD mutation. Crenolanib potently decreased the viability of Ba/F3 expressing D835Y/ITD cells with an IC50 value of 20.4 nM (Table 14). The sensitivity of crenolanib besylate was superior to that of AC220 treatment for Ba/F3 D835Y/ITD expressing cells. See Galanis A, Rajkhowa T, Muralidhara C, et al. Crenolanib: A next generation FLT3 inhibitor. Cancer Research. 2012; 72(8 Supplement): 3660.

TABLE 13

Potency of the besylate salt of the present invention compared to AC220, another FLT3 TKI known in the art, Ba/F3 cells with a double FLT3 D835Y/FLT3 ITD mutation.

| Cell line | Crenolanib IC50 pFLT3 | AC220 IC50 pFLT3 |
|---|---|---|
| Ba/F3 D835Y/ITD | 20.4 nM | 125 nM |

Biological Data for Type I FLT3 TKI Crenolanib Besylate Overcoming Resistance Associated with a Type II FLT3 TKI.

The ability of crenolanib besylate to inhibit FLT3 D835V signaling in a primary AML patient blast sample was determined via MTT assay. The sample was taken from a 53 year old male diagnosed with FLT3 ITD AML following prior treatment to induction and salvage chemotherapy. He was treated with AC220, a type II FLT3 inhibitor known in the art, achieved a response, underwent an allogeneic transplant, and then went into remission. Four months following the transplant, the patient relapsed. The patient then harbored both a FLT3 ITD and FLT3 D835Y mutation. H is blasts were incubated for 3 days in culture medium with crenolanib besylate and sorafenib. Crenolanib overcame the type II FLT3 TKI resistance and induced a cytotoxic effect, while sorafenib was ineffective. See Galanis A, Rajkhowa T, Ramachandran A, et al. Crenolanib is a highly potent, selective, FLT3 TKI with activity against D835 mutations. Blood. 2012; 120: 1341.

Biological Data for Combining the Besylate Salt of the Present Invention with Cytotoxic Chemotherapy.

The effect of crenolanib on nucleoside analogue uptake in AML cells was evaluated. Cells were incubated for 2 hours with 1.25 uM of radiolabeled cytarabine combined with DMSO control or in combination with crenolanib at 0.1 uM for 5 minutes and 2 hours. Combining cytarabine with crenolanib in FLT3 wild-type OCI-AML3 cells and FLT3-ITD MV411 cells showed that crenolanib does not decrease cytarabine accumulation in AML cells, despite length of crenolanib incubation time. Synergistic in vitro anti-leukemic effects are observed when crenolanib besylate and cytarabine are combined in vitro in MV-411 FLT3 ITD cells.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Muralidhara C, Ramachandran A, Jain V. Crenolanib, a novel type I, mutant-specific inhibitor of class III receptor tyrosine kinases, preferentially binds to phosphorylated kinases. Cancer Research. 2012; 72 (8 Supplement): 3683.

Drexler, H G et al. Expression of FLT3 receptor and response to FLT3 ligand by leukemic cells. Leukemia. 1996; 10:588-599.

Gilliland, D G and J D Griffin. The roles of FLT3 in hematopoiesis and leukemia. Blood. 2002; 100:1532-1542.

Stirewalt, D L and J P Radich. The role of FLT3 in hematopoietic malignancies. Nat Rev Cancer. 2003; 3:650-665.

Nakao M, S Yokota and T Iwai. Internal tandem duplication of the FLT3 gene found in acute myeloid leukemia. Leukemia. 1996; 10:1911-1918.

H Kiyoi, M Towatari and S Yokota. Internal Tandem duplication of the FLT3 gene is a novel modality of elongation mutation which causes constitutive activation of the product. Leukemia. 1998; 12:1333-1337.

P D Kottaridis, R E Gale, et al. The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. Blood. 2001; 98:1742-1759.

Yamamoto Y, Kiyoi H, Nakano Y. Activating mutation of D835 within the activation loop of FLT3 in human hematologic malignancies. Blood. 2001; 97:2434-2439.

Thiede C, C Steudel, Mohr B. Analysis of FLT3-activating mutations in 979 patients with acute myelogenous leukemia: association with FAB subtypes and identification of subgroups with poor prognosis. Blood. 2002; 99:4326-4335.

S Bains, Luthra R, Medeiros L J and Zuo Z. FLT3 and NPM1 mutations in myelodysplastic syndromes: Frequency and potential value for predicting progression to acute myeloid leukemia. American Journal of Clinical Pathology. January 2011; 135:62-69.

P K Bhamidipati, Daver N G, Kantarjian H, et al. FLT3 mutations in myelodysplastic syndromes(MDS) and chronic myelomonocytic leukemia (CMML). 2012. Journal of Clinical Oncology. Suppl; abstract 6597.

Nakao M, S Yokota and T Iwai. Internal tandem duplication of the FLT3 gene found in acute myeloid leukemia. Leukemia. 1996; 10:1911-1918.

H Kiyoi, M Towatari and S Yokota. Internal Tandem duplication of the FLT3 gene is a novel modality of elongation mutation which causes constitutive activation of the product. Leukemia. 1998; 12:1333-1337.

H Kiyoi, T Naoe and S Yokota. Internal tandem duplication of FLT3 associated with leukocytosis in acute promyelocytic leukemia. Leukemia Study Group of the Ministry of Health and Welfare (Kohseisho). Leukemia. 1997; 11:1447-1452.

S Schnittger, C Schoch and M Duga. Analysis of FLT3 length mutations in 1003 patients with acute myeloid leukemia: correlation to cytogenetics, FAB subtype, and prognosis in the AMLCG study and usefulness as a marker for the detection of minimal residual disease. Blood. 2002; 100:59-66.

F M Abu-Duhier, Goodeve A C, Wilson G A, et al. FLT3 internal tandem duplication mutations in adult acute myeloid leukemia define a high risk group. British Journal of Haematology. 2000; 111:190-195.

H Kiyoi, T Naoe, Y Nakano, et al. Prognostic implication of FLT3 and N-RAS gene mutations in acute myeloid leukemia. Blood. 1999; 93:3074-3080.

D L Stirewalt and J P Radich. The role of FLT3 in haematopoietic malignancies. Nature Reviews Cancer. 2003; 3:650-665

Y Yamamoto, H Kiyoi and Y Nakano, et al. Activating mutation of D835 within the activation loop of FLT3 in human hematologic malignancies. Blood. 2001; 97:2434-2439.

C Thiede, Steudal C, Mohr B, et al. Analysis of FLT3-activating mutations in 979 patients with acute myelogenous leukemia: association with FAB subtypes and identification of subgroups with poor prognosis. Blood. 2002; 99:4326-4335.

U Bacher, Haferlach C, W Kern, et al. Prognostic relevance of FLT3-TKD mutations in AML: the combination matters-an analysis of 3082 patients. Blood. 2008; 111:2527-2537.

T Kindler, Lipka D B, and Fischer T. FLT3 as a therapeutic target in AML: still challenging after all these years. Blood. 2010; 116:5089-102.

Liu, Y and N Gray. Rational design of inhibitors that bind to inactive kinase conformations. Nature Chem. Biol. 2006; 2:358-354.

A Ramachandran, Marshall H and Jain V. Crenolanib, a novel type I, mutant specific inhibitor of class III receptor tyrosine kinases, preferentially binds to phosphorylated kinases. Cancer Res. 2012; 72 (8 supplement): 3683.

Zhang, Yang P L, and Gray N S. Targeting cancer with small molecule kinase inhibitors. Nature Reviews Cancer. 2009; 9:28-39.

P W Manley, Cowan-Jacob S W, Mestan J. Advances in the structural biology, design and clinical development of Bcr-Abl kinase inhibitors for the treatment of chronic myeloid leukaemia. Biochim. Biophis. Acta. 2005; 1754:3-13.

P T Wan, et al. Mechanism of activation of the RAF-ERK signaling pathway by oncogenic mutations of B-RAF. Cell. 2004; 116:855-867.

Biological Procedure References

M A Fabian et al. A small molecule-kinases interaction map for clinical kinase inhibitors. Nat. Biotechnol. 2005; 23:329-336.

M W Karaman et al. A quantitative analysis of kinase inhibitor selectivity. Nat Biotechnol. 2008; 26:127-132.

T A Carter et al Inhibition of drug-resistant mutants of ABL, KIT, and EGF receptor kinases. Proc. Natl. Acad. Sci. USA. 2005; 102:11011-11016.

What is claimed is:

1. A method of inhibiting or reducing deregulated FLT3 tyrosine kinase activity or expression in a subject with a hematologic malignancy which comprises administering to the subject having or suspected to have the hematologic malignancy, a therapeutically or prophylactically effective amount of the compound of Formula 1:

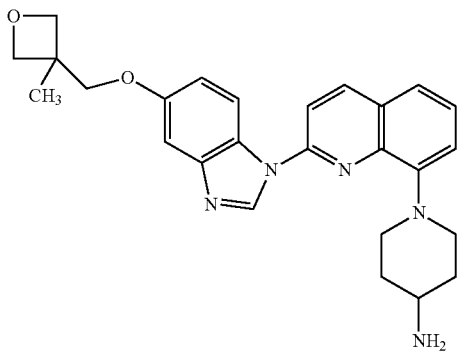 [SMILES: CC1(COc2ccc3c(c2)ncn3-c2ccc3cccc(N4CCC(N)CC4)c3n2)COC1]

or a pharmaceutically acceptable salt or solvate thereof.

2. The method of claim 1, wherein the hematologic malignancy is selected from at least one of a leukemia, a myeloma, a myeloproliferative disease, or a myelodysplastic syndrome.

3. The method of claim 1, wherein the therapeutically or prophylactically effective amounts are from about 15 to 500, 25 to 450, 50 to 400, 100 to 350, 150 to 300, 200 to 250, 15, 25, 50, 75, 100, 150, 200, 250, 300, 400, 450, or 500 mg per day.

4. The method of claim 1, wherein the compound is administered at least one of continuously, intermittently, systemically, or locally.

5. The method of claim 1, wherein deregulated FLT3 is defined further as a mutated FLT3 is constitutively active.

6. The method of claim 1, wherein the compound is administered orally, intravenously, or intraperitoneally.

7. The method of claim 1, wherein the Crenolanib is at least one of Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate Crenolanib Besylate.

8. The method of claim 1, wherein the FLT3 is at least one of FLT3-ITD or FLT3-TKD.

9. The method of claim 1, wherein the therapeutically or prophylactically effective amount of compound is administered daily for as long as the subject is in need of treatment for the hematologic malignancy.

10. The method of claim 1, wherein the compound is provided at least one of sequentially or concomitantly, with another cytotoxic or targeted pharmaceutical agent in a newly diagnosed hematologic malignancy subject, to maintain remission of an existing subject, or a relapsed/refractory hematologic malignancy subject.

11. The method of claim 1, wherein compound is provided as a single agent or in combination with another cytotoxic or targeted pharmaceutical agent in a newly diagnosed hematologic malignancy subject, to maintain remission, or a relapsed/refractory hematologic malignancy subject.

12. The method of claim 1, wherein the compound is provided as a single agent or in combination with another cytotoxic or targeted pharmaceutical agent in a newly diagnosed hematologic malignancy pediatric subject, to maintain remission, or a relapsed/refractory hematologic malignancy pediatric subject.

13. The method of claim 1, further comprising the step of determining if the subject is relapsed/refractory to a prior FLT3 tyrosine kinase inhibitor.

14. A method for treating a subject with a hematologic malignancy comprising:
administering to the subject in need of such treatment a therapeutically effective amount of Crenolanib or a salt thereof, wherein the hematologic disorder is characterized by deregulated FLT3 receptor tyrosine kinase activity, the hematologic malignancy is selected from at least one of a leukemia, a myeloma, a myeloproliferative disease, or a myelodysplastic syndrome.

15. The method of claim 14, wherein the compound is administered orally, intravenously, or intraperitoneally.

16. The method of claim 14, wherein the Crenolanib is at least one of Crenolanib Besylate, Crenolanib Phosphate, Crenolanib Lactate, Crenolanib Hydrochloride, Crenolanib Citrate, Crenolanib Acetate, Crenolanib Touluenesulphonate and Crenolanib Succinate Crenolanib Besylate.

17. The method of claim 14, wherein the FLT3 is at least one of FLT3-ITD or FLT3-TKD.

18. The method of claim 14, wherein the Crenolanib is provided at least one of sequentially or concomitantly, with chemotherapy, radiotherapy, or surgery in a newly diagnosed hematologic malignancy subject, to maintain remission, or a relapsed/refractory hematologic malignancy subject.

19. The method of claim 14, wherein the Crenolanib is provided as a single agent or in combination with chemotherapy, radiotherapy or surgery for treatment of a pediatric subject with the hematologic malignancy.

20. The method of claim 14, wherein the Crenolanib is provided as a single agent to at least one of post standard induction therapy, or high dose induction therapy, in a newly diagnosed hematologic malignancy subject.

21. The method of claim 14, wherein the Crenolanib is provided as a single agent in treatment of subjects with the hematologic malignancy that is either refractory to, or has relapsed after, standard or high dose chemotherapy, radiotherapy or surgery.

22. The method of claim 14, wherein the subject is refractory to at least one other tyrosine kinase inhibitor.

23. The method of claim 14, wherein the method further comprises the step of identifying a subject in need of treatment for a hematologic malignancy prior to treatment.

24. A method for specifically inhibiting a deregulated receptor tyrosine kinase comprising: obtaining a subject sample and determining which receptor tyrosine kinases are deregulated; and administering to a mammal in need of such treatment a therapeutically effective amount of Crenolanib or a salt thereof, wherein the deregulated receptor tyrosine kinase is a FLT3 receptor tyrosine kinase.

25. The method of claim 24, wherein the deregulated receptor tyrosine kinase is present in a hematologic malignancy selected from at least one of a leukemia, a myeloma, a myeloproliferative disease, or a myelodysplastic syndrome.

26. The method of claim 24, wherein the therapeutically and prophylactically effective amounts are from about 15 to 500 mg per day.

27. The method of claim 24, wherein the compound is administered at least one of continuously, intermittently, systemically, or locally.

28. The method of claim 24, wherein deregulated FLT3 is defined further as a mutated FLT3 is constitutively active.

29. The method of claim 24, wherein the compound is administered orally, intravenously, or intraperitoneally.

30. The method of claim 24, wherein the Crenolanib is at least one of Crenolanib Besylate, Crenolanib Phosphate, Crenolanib Lactate, Crenolanib Hydrochloride, Crenolanib Citrate, Crenolanib Acetate, Crenolanib Touluenesulphonate and Crenolanib Succinate, Crenolanib Besylate.

31. The method of claim 24, wherein the FLT3 is at least one of FLT3-ITD or FLT3-TKD.

32. The method of claim 24, wherein the therapeutically or prophylactically effective amount of the compound is administered daily for as long as the subject is in need of treatment for the hematologic malignancy.

33. The method of claim 24, wherein the subject is provided treatment, and the method further comprises the steps of: obtaining one or more subject samples to determine the effect of the treatment, and continuing treatment until the hematologic malignancy is reduced or eliminated.

34. The method of claim 24, wherein the compound is provided at least one of sequentially or concomitantly, with another cytotoxic or targeted pharmaceutical agent in a newly diagnosed hematologic malignancy subject, to maintain remission, or a relapsed/refractory hematologic malignancy subject.

35. The method of claim 24, wherein the compound is provided as a single agent or in combination with another cytotoxic or targeted pharmaceutical agent in a newly diagnosed hematologic malignancy subject, to maintain remission, or a relapsed/refractory hematologic malignancy subject.

36. The method of claim 24, wherein the compound is provided as a single agent or in combination with another cytotoxic or targeted pharmaceutical agent in a newly diagnosed pediatric subject with a hematologic malignancy, to maintain remission, or a relapsed/refractory pediatric subject with a hematologic malignancy.

37. The method of claim 24, wherein the subject is relapsed/refractory to a prior FLT3 tyrosine kinase inhibitor.

* * * * *